United States Patent

Schwalge et al.

[11] Patent Number: 4,959,098
[45] Date of Patent: Sep. 25, 1990

[54] N-SUBSTITUTED 3,4,5,6-TETRAHYDROPHTHALIMIDE DERIVATIVES

[75] Inventors: Barbara Schwalge, Ludwigshafen; Peter Plath, Frankenthal; Karl Eicken, Wachenheim; Lothar Rueb, Speyer; Bruno Wuerzer, Otterstadt; Karl-Otto Westphalen, Speyer; Norbert Meyer, Ladenburg, all of Fed. Rep. of Germany

[73] Assignee: BASF Aktiengesellschaft, Ludwigshafen, Fed. Rep. of Germany

[21] Appl. No.: 360,864

[22] Filed: Jun. 2, 1989

[30] Foreign Application Priority Data

Jun. 8, 1988 [DE] Fed. Rep. of Germany ....... 3819464

[51] Int. Cl.$^5$ .................. A01N 43/36; C07D 209/48
[52] U.S. Cl. ................................ 71/95; 71/96; 548/465
[58] Field of Search ................ 548/465; 71/95, 96

[56] References Cited

U.S. PATENT DOCUMENTS 4,420,327 12/1983 Jikihara et al. .................... 548/465
4,846,882 7/1989 Chang ................................ 548/465

FOREIGN PATENT DOCUMENTS 0240659 10/1987 European Pat. Off. .
0300398 1/1989 European Pat. Off. .
0082360 5/1984 Japan ................................ 598/465
WO87/07602 12/1987 World Int. Prop. O. .

OTHER PUBLICATIONS

Chem. Abstract 109:230,701c (Dec. 1988).
Chem. Abstract 102:24,478n (Jan. 1985).
Chem. Abstract 105:60,524v (Aug. 1986).

*Primary Examiner*—Mukund J. Shah
*Attorney, Agent, or Firm*—Keil & Weinkauf

[57] ABSTRACT

N-aryltetrahydrophthalimide compounds of the general formula I

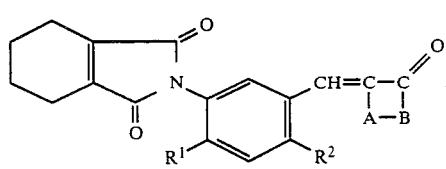

where $R^1$ is hydrogen or halogen, $R^2$ is halogen, A is substituted or unsubstituted $C_2$–$C_4$-alkylene or $C_2$–$C_4$-alkenylene, B is oxygen, sulfur or a group $NR^3$, where $R^3$ is hydrogen or substituted or unsubstituted $C_1$–$C_6$-alkyl, $C_3$–$C_7$-cycloalkyl, $C_1$–$C_4$-haloalkyl, $C_2$–$C_6$-alkenyl or $C_3$–$C_6$-alkynyl, and methods of controlling unwanted plant growth and of influencing plant growth.

9 Claims, No Drawings

N-SUBSTITUTED 3,4,5,6-TETRAHYDROPHTHALIMIDE DERIVATIVES

The present invention relates to N-aryltetrahydrophthalimide compounds of the formula I

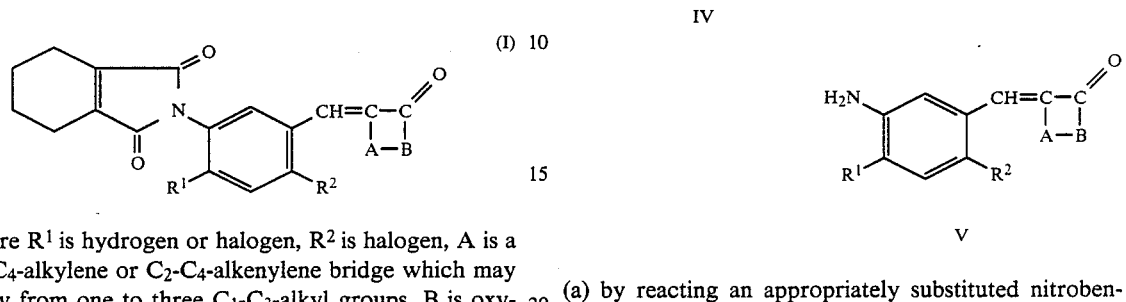

where $R^1$ is hydrogen or halogen, $R^2$ is halogen, A is a $C_2$-$C_4$-alkylene or $C_2$-$C_4$-alkenylene bridge which may carry from one to three $C_1$-$C_3$-alkyl groups, B is oxygen, sulfur or a group $NR^3$ and $R^3$ is hydrogen, $C_1$-$C_6$-alkyl, $C_3$-$C_7$-cycloalkyl, $C_1$-$C_4$-haloalkyl, $C_2$-$C_6$-alkenyl or $C_3$-$C_6$-alkynyl, and these groups may carry one of the following radicals: $C_1$-$C_4$-alkoxy, $C_1$-$C_4$-alkylthio or $C_5$-$C_7$-cycloalkyl.

The present invention furthermore relates to herbicides which contain these compounds.

EP-A No. 0 240 659 discloses compounds which have a structure similar to that of I but carry an open-chain radical instead of the radical

However, particularly for use adjacent to crops, for example by the post-emergence method, compounds which permit a low application rate and have relatively high selectivity are desirable.

It is an object of the present invention to find and to synthesize suitable active ingredients.

We have found that this object is achieved by the N-aryltetrahydrophthalimide compounds I defined at the outset.

The present invention furthermore relates to processes for the preparation of novel compounds I and their use in herbicides.

The substituted N-(heterocyclylidenemethyl)phenyl-3,4,5,6-tetrahydrophthalimide derivatives of the formula I can be obtained from tetrahydrophthalic anhydride and an appropriate aniline derivative, for example in a solvent at from 20° to 200° C., preferably from 40° to 150° C. Examples of suitable solvents are lower fatty acids, such as glacial acetic acid or propionic acid, and aprotic solvents. When an aprotic solvent is used, a water separator is advantageously employed.

The aniline derivatives of the formula V can be obtained from the corresponding nitrophenyl derivatives IV, either by reduction with, for example, tin(II) ions or iron or by catalytic hydrogenation over metal catalysts, for example Raney nickel, palladium or platinum.

The required nitrophenyl derivatives IV can be prepared by various methods, for example:

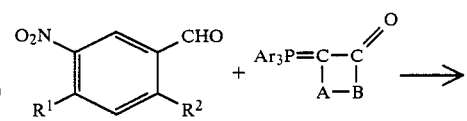

IV

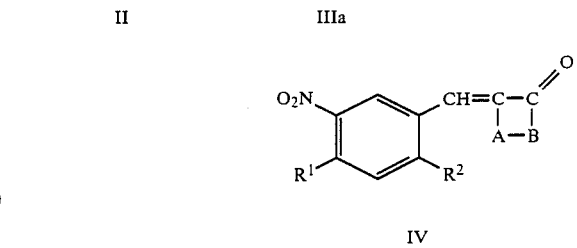

V (a) by reacting an appropriately substituted nitrobenzaldehyde of the formula II in a conventional manner, for example under the conditions described in Synthesis (10), 862 (1984), in a solvent at from room temperature to the boiling point of the solvent, with a triarylphosphorane of the formula IIIa.

In formula IIIa, Ar is an aromatic radical, preferably phenyl. Examples of suitable solvents are toluene, tetrahydrofuran, dimethylformamide, dimethyl sulfoxide and methanol.

The required triarylphosphoranes IIIa are obtainable by processes similar to those described in the literature (B=O in Helv. Chim. Acta 46 (1963), 1580; B=S in Tetrahedron Lett. 52 (1968), 5435; B=NH in DE-A-No. 2 029 43).

The preparation of the triarylphospharanes IIIa of type $B=NR^3$ where $R^3 \neq H$ is carried out similarly to J. Med. Chem. 30 (1987), 1995 or by direct bromination of the appropriately substituted lactams IX with N-bromosuccinimide, for example by the method described in Synthesis 1977, 272, followed by reaction with triphenylphosphine and base.

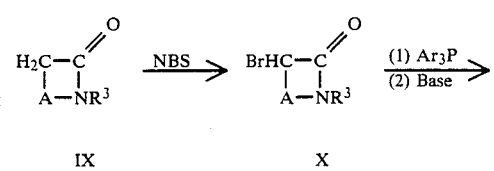

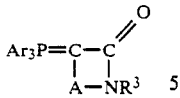

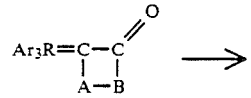

(b) by condensing an appropriately substituted nitrobenzaldehyde II with a phosphonate of the formula IIIb.

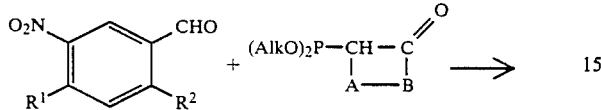

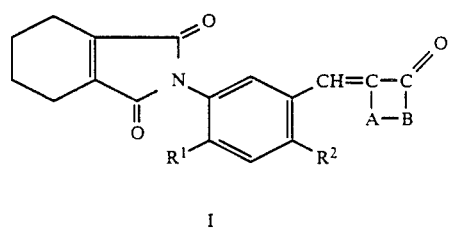

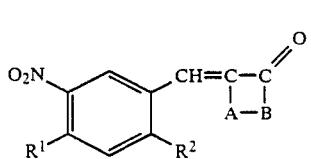

The aldehyde VIII required for this purpose is obtained by hydrogenating the corresponding nitrobenzaldehyde acetal [obtainable according to Aust. J. Chem. 23 (10) (1970), 2039] under relatively mild conditions over a noble metal catalyst or a catalyst such as Raney nickel and condensing the resulting aniline derivative VII with tetrahydrophthalic anhydride.

Conditions suitable for this reaction are described in, for example, Organic Reactions 25 (1977), 73. Either the reaction is carried out in the presence of a strong base, for example an alcoholate, a metal hydride or a metal alkyl, in an aprotic solvent, e.g. toluene, tetrahydrofuran, ether or dimethyl sulfoxide, or condensation is effected in a two-phase system with the addition of a phase-transfer catalyst, for example under the conditions described in Synthesis 1986, 926. Examples of suitable bases for this purpose are carbonates of sodium and of potassium and hydroxides of sodium, of potassium, of barium and of calcium.

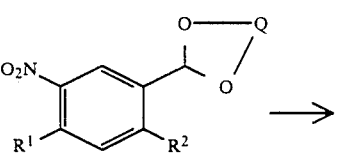

The phase-transfer catalysts used here are preferably crown ethers, such as 15-crown-5 or 18-crown-6, or corresponding benzofused derivatives, e.g. dibenzo-18-crown-6.

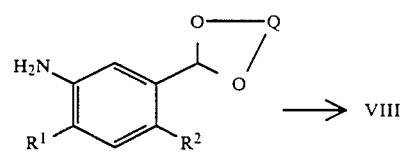

In some cases, it is also possible to use polyethylene glycol dialkyl ethers of the type

(where n is 5–7 and X and Y independently of one another are each $C_1$-$C_4$-alkyl) or quaternary ammonium salts.

However, derivatives of the formula I can also be obtained directly if triarylphosphoranes of the formula IIIa are condensed with a suitably substituted aldehyde VIII under the conditions described in (a).

In formula VI, Q is an ethylene or propylene bridge which may carry from 1 to 3 alkyl groups, preferably methyl or ethyl.

If lower fatty acids, such as glacial acetic acid or propionic acid, are used as solvents for the condensation, the acetal group is simultaneously cleaved to give the aldehyde.

Because of the biological activity, preferred compounds I are those where $R^1$ is hydrogen or halogen, such as fluorine, chlorine or bromine, particularly fluorine, $R^2$ is a halogen atom as stated for $R^1$, preferably chlorine or bromine, A is alkylene or alkenylene, such as ethylene, propylene, butylene, ethenylene, propenylene or butenylene, preferably ethylene, propylene, ethenylene or propenylene, and these radicals may be monosubstituted to trisubstituted by alkyl, such as methyl, ethyl, propyl or 1-methylethyl, in particular methyl, B is oxygen, sulfur or a group $NR^3$ and $R^3$ is hydrogen, alkyl as stated for A or n-butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl,

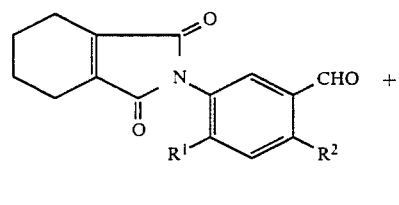

3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl,1,2,2-trimethylpropyl, 1-ethyl-1-methylpropyl or 1-ethyl-2-methylpropyl, in particular methyl, ethyl, 1-methylethyl or 1-methylpropyl, cycloalkyl, such as cyclopropyl, cyclobutyl, cyclopentyl, cyclohexyl or cycloheptyl, in particular cyclopropyl, cyclopentyl or cyclohexyl, haloalkyl, such as difluoromethyl, trifluoromethyl, 2-chloro-1,1,2-trifluoroethyl, 1,1,2,2-tetrafluoroethyl, 2,2,2-trifluoroethyl, 3-chloropropyl, 3-fluoroethyl, 2,2-difluoropropyl, 1,1,2,3,3,3-hexafluoropropyl, 4-chlorobutyl or 4-fluorobutyl, in particular difluoromethyl, trifluoromethyl or 1,1,2,2-tetrafluoroethyl, alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propeny-1, 1,2-dimethyl-2-propenyl, 1-ethyl-1-propenyl, 1-ethyl-2-propenyl, 1-hexenyl, 2-hexenyl, 3-hexenyl. 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, in particular 2-propenyl or 2-butenyl, or alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, in particular 2-propynyl or 2-butynyl, and the abovementioned radicals $R^3$ may in turn carry one of the following substituents: alkoxy, such as methoxy, ethoxy, propoxy, 1-methylethoxy, butoxy, 1-methylpropoxy, 2-methylpropoxy or 1,1-dimethylethoxy, in particular methoxy, ethoxy or 1-methylethoxy, alkylthio, such as methylthio, ethylthio, propylthio, 1-methylethylthio, butylthio, 1-methylpropylthio, 2-methylpropylthio or 1,1-dimethylethylthio, in particular methylthio or ethylthio, or one of the abovementioned $C_5$-$C_7$-cycloalkyl groups.

Examples of very active compounds I are shown in Tables A, B and C below.

TABLE A

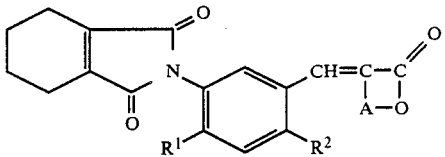

| $R^1$ | $R^2$ | A |
|---|---|---|
| H | Cl | $CH_2CH_2$ |
| F | Cl | $CH_2CH_2$ |
| H | Cl | $CH_2CH(CH_3)$ |
| F | Cl | $CH_2CH(CH_3)$ |
| H | Cl | $CH_2CH(CH_2CH_3)$ |
| F | Cl | $CH_2CH(CH_2CH_3)$ |
| H | Cl | $CH_2CH(CH_2CH_2CH_3)$ |
| F | Cl | $CH_2CH(CH_2CH_2CH_3)$ |
| H | Cl | $CH_2C(CH_3)_2$ |
| F | Cl | $CH_2C(CH_3)_2$ |
| H | Cl | $CH(CH_3)CH_2$ |
| F | Cl | $CH(CH_3)CH_2$ |
| H | Cl | $CH(CH_2CH_3)CH_2$ |
| F | Cl | $CH(CH_2CH_3)CH_2$ |
| H | Cl | $CH(CH_3)CH(CH_3)$ |
| F | Cl | $CH(CH_3)CH(CH_3)$ |
| H | Cl | $C(CH_3)_2CH_2$ |
| F | Cl | $C(CH_3)_2CH_2$ |
| H | Cl | $CH_2C(CH_2CH_3)_2$ |
| F | Cl | $CH_2C(CH_2CH_3)_2$ |
| H | Cl | $CH_2C(CH_3)(C_2H_5)$ |
| F | Cl | $CH_2C(CH_3)(C_2H_5)$ |
| H | Cl | $CH_2CH_2CH_2$ |
| F | Cl | $CH_2CH_2CH_2$ |
| H | Cl | $CH_2CH_2CH(CH_3)$ |
| F | Cl | $CH_2CH_2CH(CH_3)$ |
| H | Cl | $CH_2CH_2C(CH_3)_2$ |
| F | Cl | $CH_2CH_2C(CH_3)_2$ |
| H | Cl | $CH_2CH(CH_3)CH_2$ |
| F | Cl | $CH_2CH(CH_3)CH_2$ |
| H | Cl | $CH_2C(CH_3)_2CH_2$ |
| F | Cl | $CH_2C(CH_3)_2CH_2$ |
| H | Cl | $CH(CH_3)CH_2CH_2$ |
| F | Cl | $CH(CH_3)CH_2CH_2$ |
| H | Cl | $C(CH_3)_2CH_2CH_2$ |
| F | Cl | $C(CH_3)_2CH_2CH_2$ |
| H | Cl | $CH(CH_3)CH(CH_3)CH_2$ |
| F | Cl | $CH(CH_3)CH(CH_3)CH_2$ |
| H | Cl | $CH_2CH(CH_3)CH(CH_3)$ |
| F | Cl | $CH_2CH(CH_3)CH(CH_3)$ |
| H | Cl | $CH(CH_3)CH(CH_3)CH(C_2H_5)$ |
| F | Cl | $CH(CH_3)CH(CH_3)CH(C_2H_5)$ |
| H | Cl | $CH_2CH_2CH(C_3H_7)$ |
| F | Cl | $CH_2CH_2CH(C_3H_7)$ |
| H | Cl | $CH_2CH_2CH_2CH_2$ |
| F | Cl | $CH_2CH_2CH_2CH_2$ |
| H | Cl | $CH=CH$ |
| F | Cl | $CH=CH$ |
| H | Cl | $CH=C(CH_3)$ |
| F | Cl | $CH=C(CH_3)$ |
| H | Cl | $CH=C(C_2H_5)$ |
| F | Cl | $CH=C(C_2H_5)$ |
| H | Cl | $CH=CHCH_2$ |
| F | Cl | $CH=CHCH_2$ |
| H | Cl | $CH=C(CH_3)CH_2$ |
| F | Cl | $CH=C(CH_3)CH_2$ |
| H | Cl | $CH_2C(CH_3)=CH$ |
| F | Cl | $CH_2C(CH_3)=CH$ |
| H | Cl | $CH_2CH=CH$ |
| F | Cl | $CH_2CH=CH$ |
| H | Cl | $CH(CH_3)CH=CH$ |
| F | Cl | $CH(CH_3)CH=CH$ |
| H | Cl | $C(CH_3)_2CH=CH$ |
| F | Cl | $C(CH_3)_2CH=CH$ |
| H | Cl | $CH=CHCH_2CH_2$ |
| F | Cl | $CH=CHCH_2CH_2$ |

TABLE B

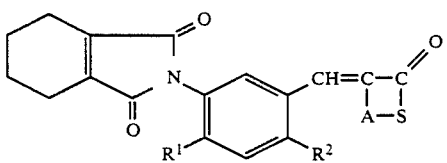

| R¹ | R² | A |
|---|---|---|
| H | Cl | CH₂CH₂ |
| F | Cl | CH₂CH₂ |
| H | Cl | CH₂CH(CH₃) |
| F | Cl | CH₂CH(CH₃) |
| H | Cl | CH(CH₃)CH₂ |
| F | Cl | CH(CH₃)CH₂ |
| H | Cl | CH(CH₃)CH(CH₃) |
| F | Cl | CH(CH₃)CH(CH₃) |
| H | Cl | CH₂CH₂CH₂ |
| F | Cl | CH₂CH₂CH₂ |
| H | Cl | CH(CH₃)CH₂CH₂ |
| F | Cl | CH(CH₃)CH₂CH₂ |
| H | Cl | CH₂CH₂CH₂CH₂ |
| F | Cl | CH₂CH₂CH₂CH₂ |
| H | Cl | CH=CH |
| F | Cl | CH=CH |
| H | Cl | CH=C(CH₃) |
| F | Cl | CH=C(CH₃) |
| H | Cl | CH=C(C₂H₅) |
| F | Cl | CH=C(C₂H₅) |
| H | Cl | CH₂CH=CH |
| F | Cl | CH₂CH=CH |
| H | Cl | CH₂C(CH₃)=CH |
| F | Cl | CH₂C(CH₃)=CH |
| H | Cl | CH₂CH₂CH₂CH₂ |
| F | Cl | CH₂CH₂CH₂CH₂ |

TABLE C

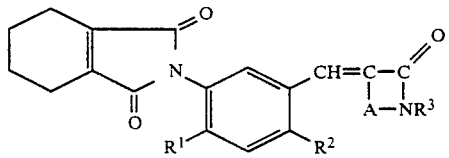

| R¹ | R² | A | R³ |
|---|---|---|---|
| H | Cl | CH₂CH₂ | H |
| F | Cl | CH₂CH₂ | H |
| H | Cl | CH₂CH(CH₃) | CH₃ |
| F | Cl | CH₂CH(CH₃) | CH₃ |
| H | Cl | CH₂CH(CH₂CH₃) | CH₃ |
| F | Cl | CH₂CH(CH₂CH₃) | CH₃ |
| H | Cl | CH₂CH(CH₂CH₂CH₃) | CH₃ |
| F | Cl | CH₂CH(CH₂CH₂CH₃) | CH₃ |
| H | Cl | CH₂C(CH₃)₂ | CH₃ |
| F | Cl | CH₂C(CH₃)₂ | CH₃ |
| H | Cl | CH(CH₃)CH₂ | CH₃ |
| F | Cl | CH(CH₃)CH₂ | CH₃ |
| H | Cl | CH(CH₂CH₃)CH₂ | CH₃ |
| F | Cl | CH(CH₂CH₃)CH₂ | CH₃ |
| H | Cl | CH(CH₃)CH(CH₃) | CH₃ |
| F | Cl | CH(CH₃)CH(CH₃) | CH₃ |
| H | Cl | C(CH₃)₂CH₂ | CH₃ |
| F | Cl | C(CH₃)₂CH₂ | CH₃ |
| H | Cl | CH₂C(CH₂CH₃)₂ | CH₃ |
| F | Cl | CH₂C(CH₂CH₃)₂ | CH₃ |
| H | Cl | CH₂C(CH₃)(C₂H₅) | CH₃ |
| F | Cl | CH₂C(CH₃)(C₂H₅) | CH₃ |
| H | Cl | CH₂CH₂CH₂ | H |
| F | Cl | CH₂CH₂CH₂ | H |
| H | Cl | CH₂CH₂CH₂ | CH₃ |
| F | Cl | CH₂CH₂CH₂ | CH₃ |
| H | Cl | CH₂CH₂CH₂ | CH=CH₂ |
| F | Cl | CH₂CH₂CH₂ | CH=CH₂ |
| H | Cl | CH₂CH₂CH(CH₃) | CH₃ |
| F | Cl | CH₂CH₂CH(CH₃) | CH₃ |
| H | Cl | CH₂CH₂C(CH₃)₂ | CH₃ |

TABLE C-continued

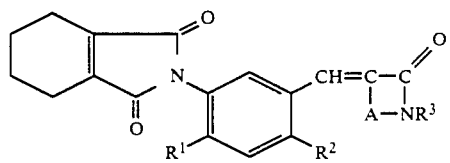

| R¹ | R² | A | R³ |
|---|---|---|---|
| F | Cl | CH₂CH₂C(CH₃)₂ | CH₃ |
| H | Cl | CH₂CH(CH₃)CH₂ | CH₃ |
| F | Cl | CH₂CH(CH₃)CH₂ | CH₃ |
| H | Cl | CH₂C(CH₃)₂CH₂ | CH₃ |
| F | Cl | CH₂C(CH₃)₂CH₂ | CH₃ |
| H | Cl | CH(CH₃)CH₂CH₂ | CH₃ |
| F | Cl | CH(CH₃)CH₂CH₂ | CH₃ |
| H | Cl | C(CH₃)₂CH₂CH₂ | CH₃ |
| F | Cl | C(CH₃)₂CH₂CH₂ | CH₃ |
| H | Cl | CH(CH₃)CH(CH₃)CH₂ | CH₃ |
| F | Cl | CH(CH₃)CH(CH₃)CH₂ | CH₃ |
| H | Cl | CH₂CH(CH₃)CH(CH₃) | CH₃ |
| F | Cl | CH₂CH(CH₃)CH(CH₃) | CH₃ |
| H | Cl | CH(CH₃)CH(CH₃)CH(C₂H₅) | CH₃ |
| F | Cl | CH(CH₃)CH(CH₃)CH(C₂H₅) | CH₃ |
| H | Cl | CH₂CH₂CH(C₃H₇) | CH₃ |
| F | Cl | CH₂CH₂CH(C₃H₇) | CH₃ |
| H | Cl | CH₂CH₂CH₂CH₂ | CH₃ |
| F | Cl | CH₂CH₂CH₂CH₂ | CH₃ |
| H | Cl | CH₂CH₂CH₂CH₂ | H |
| F | Cl | CH₂CH₂CH₂CH₂ | H |
| H | Cl | CH₂CH₂CH₂CH₂ | CH=CH₂ |
| F | Cl | CH₂CH₂CH₂CH₂ | CH=CH₂ |
| H | Cl | CH=CH | CH₃ |
| F | Cl | CH=CH | CH₃ |
| H | Cl | CH=C(CH₃) | CH₃ |
| F | Cl | CH=C(CH₃) | CH₃ |
| H | Cl | CH=C(C₂H₅) | CH₃ |
| F | Cl | CH=C(C₂H₅) | CH₃ |
| H | Cl | CH=CHCH₂ | CH₃ |
| F | Cl | CH=CHCH₂ | CH₃ |
| H | Cl | CH=C(CH₃)CH₂ | CH₃ |
| F | Cl | CH=C(CH₃)CH₂ | CH₃ |
| H | Cl | CH₂C(CH₃)=CH | CH₃ |
| F | Cl | CH₂C(CH₃)=CH | CH₃ |
| H | Cl | CH₂CH=CH | CH₃ |
| F | Cl | CH₂CH=CH | CH₃ |
| H | Cl | CH(CH₃)CH=CH | CH₃ |
| F | Cl | CH(CH₃)CH=CH | CH₃ |
| H | Cl | C(CH₃)₂CH=CH | CH₃ |
| F | Cl | C(CH₃)₂CH=CH | CH₃ |
| H | Cl | CH=CHCH₂CH₂ | CH₃ |
| F | Cl | CH=CHCH₂CH₂ | CH₃ |
| H | Cl | CH₂CH₂ | CH₃ |
| F | Cl | CH₂CH₂ | CH₃ |
| H | Cl | CH₂CH₂ | CHF₂ |
| F | Cl | CH₂CH₂ | CHF₂ |
| H | Cl | CH₂CH₂ | CF₃ |
| F | Cl | CH₂CH₂ | CF₃ |
| H | Cl | CH₂CH₂ | CH₂CH₃ |
| F | Cl | CH₂CH₂ | CH₂CH₃ |
| H | Cl | CH₂CH₂ | CF₂CHF₂ |
| F | Cl | CH₂CH₂ | CF₂CHF₂ |
| H | Cl | CH₂CH₂ | CH₂CH₂OCH₃ |
| F | Cl | CH₂CH₂ | CH₂CH₂OCH₃ |
| H | Cl | CH₂CH₂ | CH₂SCH₃ |
| F | Cl | CH₂CH₂ | CH₂SCH₃ |
| H | Cl | CH₂CH₂ | CH₂CH₂OCH₂CH₃ |
| F | Cl | CH₂CH₂ | CH₂CH₂OCH₂CH₃ |
| H | Cl | CH₂CH₂ | CH₂CH₂SCH₂CH₃ |
| F | Cl | CH₂CH₂ | CH₂CH₂SCH₂CH₃ |
| H | Cl | CH₂CH₂ | 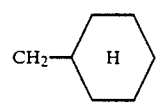 |

TABLE C-continued

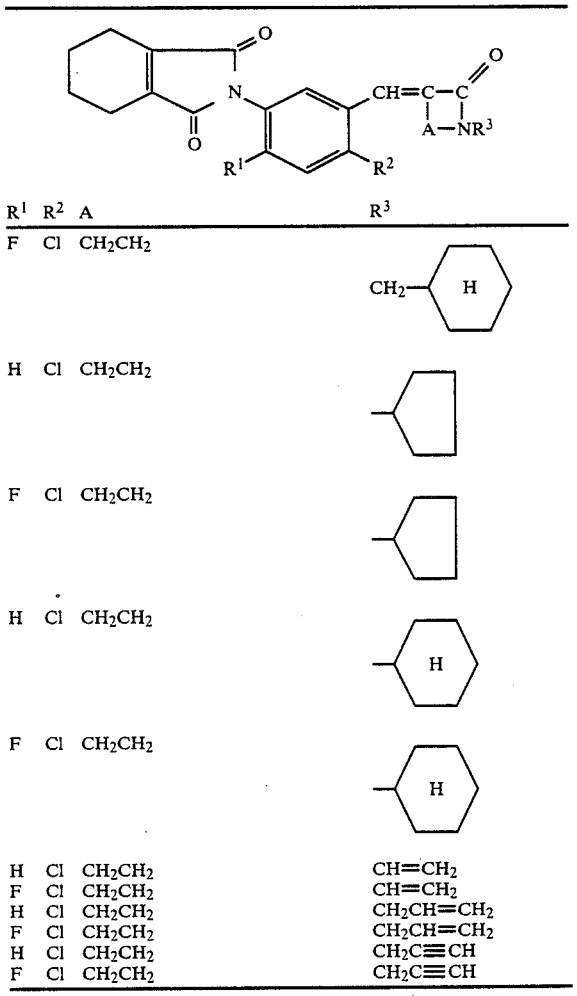

| R¹ | R² | A | R³ |
|----|----|----|----|
| F | Cl | CH₂CH₂ | CH₂–⟨C₆H₁₁⟩ |
| H | Cl | CH₂CH₂ | –⟨C₅H₉⟩ |
| F | Cl | CH₂CH₂ | –⟨C₅H₉⟩ |
| H | Cl | CH₂CH₂ | –⟨C₆H₁₁⟩ |
| F | Cl | CH₂CH₂ | –⟨C₆H₁₁⟩ |
| H | Cl | CH₂CH₂ | CH=CH₂ |
| F | Cl | CH₂CH₂ | CH=CH₂ |
| H | Cl | CH₂CH₂ | CH₂CH=CH₂ |
| F | Cl | CH₂CH₂ | CH₂CH=CH₂ |
| H | Cl | CH₂CH₂ | CH₂C≡CH |
| F | Cl | CH₂CH₂ | CH₂C≡CH |

The N-aryltetrahydrophthalmide compounds I, or the herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthlenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehide, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.5 to 95, and preferably 0.5 to 90%, by weight of active ingredient. The active ingredients are used in a purity of from 90 to 100 and preferably from 95 to 100%, (according to the NMR spectrum.

The compounds I according to the invention may be formulated for example as follows.

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 1.003 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 2.001 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.002 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 2.001 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.001 is intimately mixed with 97 parts by weight of particulate kaolin. A dust is obtained containing 3% by weight of the active ingredient.

VII. 30 parts by weight of compound no. 1.002 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 2.001 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may be applied pre- or post-emergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 5.0, preferably 0.01 to 1.0, kg of active ingredient per hectare.

The N-aryltetrahydrophthalimides of the formula I may also have a variety of influences on practically all plant development stages, and may therefore be used as growth regulators. The diversity of action of growth regulators depends especially on (a) the type and variety of plant;
(b) the time applied with reference to the development stage of the plant and the time of the year;
(c) the place and method of application (seed treatment soil treatment, or foliage application);
(d) climatic factors, e.g., temperature, amount of precipitate, day length and light intensity;
(e) soil conditions (including fertilization);
(f) the formulation of the active ingredient; and
(g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

In fruit trees and bushes, and other trees and shrubs, cost-intensive pruning can be reduced.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

The use of compounds I may also increase or inhibit lateral branching. This is of interest when, for instance in tobacco plants, it is desired to inhibit the formation of lateral shoots (suckers) in favor of leaf development.

With compounds I, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with growth-regulating agents based on the N-aryltetrahydrophthalimides I. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The N-aryltetrahydrophthalimides of the formula I may raise the yield by influencing plant metabolism or by promoting or inhibiting vegetative and/or generative plant growth.

C. It is also possible with the aryltetrahydrophthalimides I to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes drupes and indehiscent fruit. The same mechanism, i.e., promotion of the formation of separation layers between fruit or leaf and stem of the plant, is also essential for a readily controllable defoliation of crop plants.

Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients to be used in accordance with the invention may be applied not only to the seed (as a disinfectant), but also to the soil, i.e., via the roots, and to the foliage.

In view of the number of application methods possible, the compounds according to the invention, or agents containing them, may be used in a further large number of crops for removing unwanted plants. The following crops are given by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabia (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaris vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |

-continued

| Botanical name | Common name |
|---|---|
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (S. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn |

To increase the spectrum of action and to achieve synergistic effects, the N-aryltetrahydrophthalimides I may be mixed and applied together with numerous representatives of other herbicidal or growth-regulating active ingredient groups. Examples of suitable components are diazines, 4H-3, 1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, aryloxy- or heteroaryloxy-phenylpropionic acids and salts, esters and amides thereof, etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

Synthesis examples

The directions given in the synthesis examples below were used, after appropriate modification of the starting materials, to obtain further compounds I. The compounds thus obtained are listed in the tables below with physical data.

EXAMPLE 1

N-[4-Chloro-3-(4'-methyl-2'-oxo-3'-oxa-cyclopentylidenemethyl]-phenyl-3.4.5.6-tetrahydrophthalimide

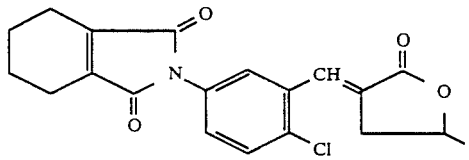

(a) At 0°–5° C. and while stirring, 7.1 g (0.03 mol) of 4-2-oxo-3-oxa-cyclopentyl-diethylphosphonate [Z. Naturforsch. B. 38B (4), 493 (1983)] in 8 ml of absolute tetrahydrofuran is added to a mixture of 7.4 g (0.054 mol) of potassium carbonate and 3.5 g (0.0135 mol) of 18-crown-6 in 10 ml of absolute tetrahydrofuran. After about 30 minutes, 5.0 g (0.027 mol) of 2-chloro-5-nitrobenzaldehyde in 6 ml of absolute tetrahydrofuran is added and the mixture is stirred for 15 hours at room temperature. The mixture is then poured into 40 ml of ice water and extracted several times with Et₂O. The organic phase is washed with 10% strength HCl and H₂O, and dried the solvent is evaporated off, and the product is separated on silica gel using toluene/acetone (9:1) as eluant. There is obtained 1.7 g of 2-(4'-methyl-2'-oxo-3'-oxa-cyclopentylidenemethyl-4-nitrochlorobenzene (mp. 87°–103° C., isomer mixture).

(b) while stirring and at 60° C., 2.4 g (0.009 mol) of 2-(4'-Methyl-2'-oxo-3'-oxa-cyclopentylidenemethyl)-4-nitrochlorobenzene in 10 ml of glacial acetic acid and 10 ml of methanol is added over a period of 15 minutes to a mixture of 3.0 g (0.054 mol) of iron powder, 7.5 ml of glacial acetic acid and 15 ml of methanol. After all has been added the mixture is refluxed for 30 minutes, cooled to room temperature, filtered and the solvent removed under reduced pressure. The residue is taken up with ethyl acetate, washed twice with NaHCO₃ solution and twice with H₂O, dried over MgSO₄ and concentrated in a rotary evaporator. There is thus obtained 2.3 g of crude 4-amino-2-(4'-methyl-2'-oxo-3'-oxa-cyclopentylidenemethyl)-chlorobenzene which is reacted without any further working up.

(c) 2.2 g 0.009 mol of 4-amino-2-(4'-methyl-2'-oxo-3'-oxa-cyclopentylidenemethyl-chlorobenzene, 1.4 g (0.009 mol) of 3.4.5.6-tetrahydrophthalic anhydride and 25 ml of glacial acetic acid are refluxed for 2 hours. After the mixture has been cooled to room temperature, the solvent is stripped off and the mixture remaining is taken up in 100 ml of ethyl acetate, washed twice with NaHCO₃ solution and twice with H₂O, dried over MgSO₄ and concentrated in a rotary evaporator. There is obtained 3.5 g of crude product which after chromatography on silica gel using toluene:acetone (98:2), gives 2.5 g of N-[4-chloro-3-(4'-methyl-2'-oxo-3'-oxa-cyclopentylidenemethyl)phenyl]-3.4.5.6-tetrahydrophthalimide. (Mp. 98°–113° C.; active ingredient example no. 1.003)

EXAMPLE 2

N-[4-Chloro-3-(2'-oxo-3'-oxa-cyclopentylidenemethyl)]-phenyl-3.4.5.6-tetrahydrophthalimide

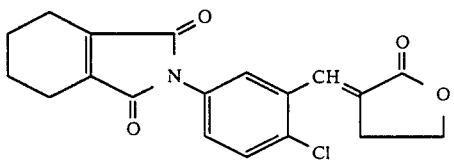

(a) A mixture of 3.4 g (0.01 mol) of 2-oxo-3-oxa-cyclopentylidenetriphenylphosphorane [Helv. Chim. Acta. 46, 1580 (1963)] and 46 g (0.01 mol) of 2-chloro-5-nitrobenzaldehyde in 150 ml of absolute dimethylformamide is heated, while stirring, for 18 hours at 110° C. After the mixture has cooled it is poured into 0.5 liters of ice water and the precipitate which forms is filtered off. After drying, there is obtained 1.1 g of 4-nitro-2-(2'-oxo-3'-oxacyclopentylidenemethyl)chlorobenzene (mp.: 157°–161° C.).

(b) 3.1 g (0.012 mol) of 4-nitro-2-(2'-oxo-3'-oxacyclopentylidenemethyl)chlorobenzene is reduced with 2.3 g of iron powder in a total of 14 ml of glacial acetic acid and 45 ml of methanol analogously to Example (1b). Working up gives 2.1 g of 4-amino-2-(2'-oxo-3'-oxacyclopentyldenemethyl)-chlorobenzene in the form of an oil which is reacted without further purification.

(c) While stirring, 2.4 g (0.011 mol) of 4-amino-2-(2'-oxo-3'-oxacyclopentylidenemethyl)-chlorobenzene and 1.6 g (0.011 mol) of 3.4.5.6-tetrahydrophthalic anhydride are refluxed in 25 ml of concentrated acetic acid for 5 hours. After the mixture has cooled the product is filtered off, washed with a small amount of H₂O and NaHCO₃ solution and dried. There is thus obtained 2.3 g of N-[4-chloro-3-(2'-oxo-3'-oxacyclopeniylidenemethyl)]-phenyl-3.4.5.6-tetrahydrophthalimide (mp.: 176°–180° C.; active ingredient example no. 1.001).

EXAMPLE 3

N-[14-Chloro-3-(2'-oxo-3'-thiacyclopentylidenemethyl)]-phenyl-3.4.5.6-tetrahydrophthalimide

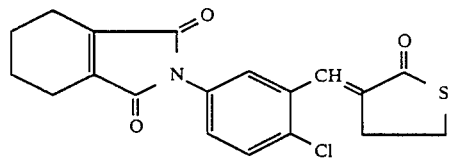

(a) 371 g (2.00 mol) of 2-chloro-5-nitrobenzaldehyde, 137 g (2.20 mol) of ethylene glycol and 1.00 g of p-toluenesulfonic acid are refluxed in 1,500 ml of toluene for 5 hours water being removed. Cooling to room temperature and concentration under reduced pressure gives 459 g (100%) of 2-(2-chloro-5-nitro)-phenyl-1.3-dioxolane; mp. 88°–90° C.

(b) 115 g 0.50 mol of the compound prepared in Example (3a) is hydrogenated in 1 000 ml of THF after the addition of 20 g of Raney nickel at a superatmospheric pressure of 0.05 bar and a temperature of 50° C. Yield: 99.0 g (99%) of 2-(5-amino-2-chloro)-phenyl-1,3-dioxolane (oil).

(c) 99.8 g (0.50 mol) of the product from Example (3b) and 76.1 g (0.50 mol) of 3.4.5.6-tetrahydrophthalic anhydride are refluxed in 500 ml of glacial acetic acid for 5 hours. After the mixture has cooled to room temperature 500 ml of water is added, and the precipitate which forms is filtered off, washed with H₂O and dried, Yield: 120 g (83%) of N-(4-chloro-3-formyl)-phenyl-3.4.5.6-tetrahydrophthalimide; mp. 140°–141° C.

(d) While stirring, mixture of 3.6 g (0.01 mol) of 2-oxo-3-thiacyclopentylidenetriphenylphosphorane [THL 52, 5435 (1968)] and 2.9 g (0.01 mol) of N-(4-chloro-3-formyl)-phenyl-3.4.5.6-tetrahydrophthalimide in 100 ml of absolute methanol is refluxed for 8 hours. After the mixture has cooled, the solvent is stripped off and the residue is separated on silica gel using toluene/cyclohexane (9:1) as eluant. There is obtained 1.3 g of N-[4-chloro-3-(2'-oxo-3'-thiacyclopentylidenemethyl)]-phenyl-3.4.5.6-tetrahydrophthalimide (yellow oil; active ingredient example no. 2.001).

EXAMPLE 4

N-[4-Chloro-2-fluoro-5-(2'-oxo-3'-oxacyclopentylidenemethyl)]-phenyl-3.4.5.6-tetrahydrophthalimide

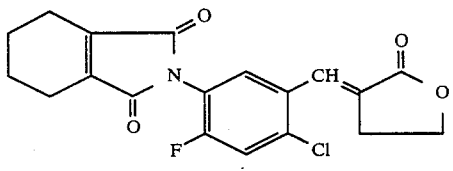

(a) Analogously to Examples 3(a)–(c), 2-chloro-4-fluoro-5-nitrobenzaldehyde can be converted by acid-catalyzed reaction with propane-1.3-diol into 2-(2-chloro-4-fluoro-5-nitro)-phenyl-1.3-dioxane (mp. 104°–105° C.), which can be reduced in the presence of Raney nickel to 2-(5-amino-2-chloro-4-fluoro)-phenyl-1.3-dioxane (mp. 80°–82° C.). Subsequent condensation with 3:4.5.6-tetrahydrophthalic anhydride in glacial acetic acid gives the desired N-(4-chloro-2-fluoro-5-formyl)-phenyl-3,4,5,6-tetrahydrophthalimide (mp.: 131°–132° C.).

(b) Analogously to Example (3d), 3.5 g (0.01 mol) of 2-oxo-3-oxacyclopentylidenetriphenylphosphorane and 3.1 g (0.01 mol) of N-(4-chloro-2-fluoro-5-formyl)-phenyl-3.4.5.6-tetrahydrophthalimide give, after stirring under reflux for 5 hours in 100 ml of absolute methanol and chromatography on silica gel using toluene/cyclohexane (9:1), 1.6 g of N-[4-chloro-2-fluoro-5-(2'-oxo-3'-oxacyclopentylidenemethyl)]-phenyl-3,4,5,6-tetrahydrophthalimide (mp.: 89°–118° C.; active ingredient example no. 1.002).

TABLE 1

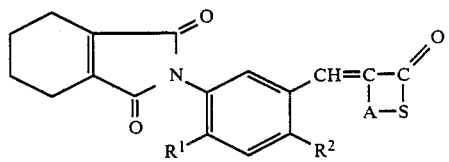

| No.   | R¹ | R² | A         | Mp.        |
|-------|----|----|-----------|------------|
| 1.001 | H  | Cl | CH₂CH₂    | 176–180° C.|
| 1.002 | F  | Cl | CH₂CH₂    | 89–118° C. |
| 1.003 | H  | Cl | CH₂CH(CH₃)| 98–113° C. |

TABLE 2

| No.   | R¹ | R² | A      | Mp. |
|-------|----|----|--------|-----|
| 2.001 | H  | Cl | CH₂CH₂ | oil |

USE EXAMPLES

The action of the N-aryltetrahydrophthalimides of the formula I is demonstrated by the following greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the active ingredients suspended or emulsified in water. In this treatment method, either plants which had been sown in the pots and grown there were selected, or they were cultivated separately as seedlings and transplanted to the pots a few days before being treated. The application rates for postemergence treatment were 0.125 and 0.06 kg/ha. No covers were placed on the vessels in this method.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments were *Abutilon theophrasti Amaranthus retroflexus, rassia tora, Chenopodium album, Chrysanthemum corinarium, Galium aparine, Solanum nigrum, Stellaria media, Triticum aestivum* (spring wheat) and *Triticum aestivum* (winter wheat).

Compounds nos. 1.001 and 1.003, applied postemergence at a rate of 0.06 kg/ha, combated unwanted plants excellently, and were tolerated by spring wheat.

Compound no. 1.001, when applied postemergence at a rate of 0.125 kg/ha, has a herbicidal action on *Stellaria media* and *Galium aparine*.

We claim:
1. An N-aryltetrahydrophthalimide compound of the formula I

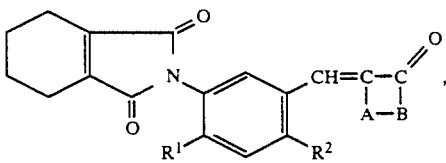

where $R^1$ is hydrogen or halogen, $R^2$ is halogen, A is a $C_2$-$C_4$-alkylene or $C_2$-$C_4$-alkenylene bridge which may carry from one to three $C_1$-$C_3$-alkyl groups and B is oxygen or sulfur.

2. A process for combating the growth of unwanted plants, wherein the unwanted plants and/or their habitat are treated with a herbicidally effective amount of an N-aryltetrahydrophthalimide compound I as set forth in claim 1.

3. A process for influencing plant growth, wherein the plants, their seed or their habitat are treated with an amount affecting growth regulation of an N-aryltetrahydrophthalimide compound I as set forth in claim 1.

4. A herbicidal composition which comprises a carrier or diluent and a herbicidally effective amount of a compound of the formula I as set forth in claim 1.

5. The compound of claim 1 which is N-[4-chloro-3-(4'-methyl-2'-oxo-3'-oxa-cyclopentylidenemethyl]-phenyl-3,4,5,6-tetrahydrophthalimide.

6. The compound of claim 1 which is N-[4-chloro-3-(2'-oxo-3'-oxa-cyclopentylidenemethyl]-phenyl-3,4,5,6-tetrahydrophthalimide.

7. The compound of claim 1 which is N-[4-chloro-3-(2'-oxo-3'-thiacyclopentylidenemethyl]-phenyl-3,4,5,6-tetrahydrophthalimide.

8. The compound of claim 1 which is N-[4-chloro-2-fluoro-5-(2'-oxo-3'-oxacyclopentylidenemethyl]-phenyl-3,4,5,6-tetrahydrophthalimide.

9. The compound of claim 1 wherein A is $C_2$-alkylene which may carry from one to three $C_1$-$C_3$-alkyl groups.